(12) United States Patent
Chu et al.

(10) Patent No.: US 6,348,491 B1
(45) Date of Patent: Feb. 19, 2002

(54) OIL-IN-WATER EMULSION FOR ENCAPSULATING PACLITAXEL

(75) Inventors: I-Ming Chu, Hsinchu; Tzy-Rong Wang, Tainan, both of (TW)

(73) Assignee: National Science Council, Taipei (TW)

( * ) Notice: Subject to any disclaimer, the term of this patent is extended or adjusted under 35 U.S.C. 154(b) by 0 days.

(21) Appl. No.: 09/430,451

(22) Filed: Oct. 29, 1999

(30) Foreign Application Priority Data

Jul. 1, 1999 (TW) .......................................... 88111153

(51) Int. Cl.$^7$ ............................................. A61K 31/335
(52) U.S. Cl. ......................................... 514/449; 514/76
(58) Field of Search ................................... 514/449, 76

(56) References Cited

U.S. PATENT DOCUMENTS

| 5,407,683 A | 4/1995 | Shively ....................... 424/439 |
| 5,415,869 A | 5/1995 | Straubinger et al. ........ 424/450 |
| 5,445,809 A | 8/1995 | Strobel et al. ............. 424/1.81 |
| 5,616,330 A | 4/1997 | Kaufman et al. ........... 424/400 |
| 5,665,761 A | 9/1997 | Canetta et al. ............. 514/449 |
| 5,840,757 A | 11/1998 | Dutot .......................... 514/560 |

*Primary Examiner*—Zohreh Fay
(74) *Attorney, Agent, or Firm*—Fish & Richardson P.C.

(57) ABSTRACT

An oil-in-water emulsion for encapsulating paclitaxel including (a) triglyceride, (b) emulsifier including phosphatidyl choline (PC), non-ionic surfactant and polyethyleneglycol-modified disteaoyl phosphatidylethanolamine (PEG-M-DSPE), and (c) pharmaceutically acceptable aqueous solution.

21 Claims, 4 Drawing Sheets

OIL-IN-WATER EMULSION FOR ENCAPSULATING PACLITAXEL

BACKGROUND OF THE INVENTION

1. Field of the Invention

The present invention relates to an emulsion, and in particular, relates to an oil-in-water emulsion for encapsulating paclitaxel.

2. Description of the Related Arts

Paclitaxel is a polyhydroxyl compound extracted from *Texus brevifolia,* and an effective anti-cancer drug. The major mechanism of the anti-cancer activity of the paclitaxel involves stabilizing microtubulin to inhibit the mitosis of tumor cells. Recently, many studies of paclitaxel in phase I and phase II clinical trials have been conducted. Furthermore, the paclitaxel has passed the phase III clinical trial against refractory ovarian cancer, breast cancer and melanoma cancer, and has been applied in the therapies thereof.

However, paclitaxel has low solubility in water (about 0.01 mg/ml) and no therapeutic effect if administrated orally. Thus, a suitable drug delivery system for administration is required. In clinical applications, paclitaxel is dissolved in Diluent 12, which is a carrier composed of 50% polyethoxylated castor oil (Cremophor EL) and 50% absolute ethanol, and then administrated to patients. Cremophor EL can cause hypersensitivity and may crystallize during the process of dilution.

To address the disadvantage of Diluent 12, many carriers used in injection administrations have been developed in recent years. Examples of these carriers are oil-in-water emulsion, liposome, and non-ionic surfactant micelles. As oil-in-water emulsions are bio-degradable, bio-compatible, easy for mass production and less toxic, they have been the preferred candidate for the delivery system. It is known that the above oil-in-water emulsion systems can form a more stable lipid emulsion, which is useful for encapsulating lipophilic drug, if phospholipid is added thereto. The oil-in-water emulsion functions as a vector for administration to prolong the drug-releasing rate in blood. However, a conventional oil-in-water emulsion can be absorbed easily by the endoreticular system within the body and destroyed. Accordingly, the lipophilic drug cannot be maintained at a constantly effective concentration in blood, and thus the conventional oil-in-water emulsion is not stable.

SUMMARY OF THE INVENTION

It is therefore an object of the present invention to provide an oil-in-water emulsion for encapsulating paclitaxel that can eliminate the disadvantages of the conventional oil-in-water emulsions.

The above object of the invention is attained by using an emulsion including triglyceride and emulsifier. The emulsifier includes phosphatidyl choline, non-ionic surfactant and polyethyleneglycol-modified phosphatidylethanolamine. Optionally, the emulsion of the invention can further include a pharmaceutically acceptable aqueous solution.

The surface of the oil-in-water emulsion is modified by the polyethyleneglycol-modified disteaoyl phosphatidylethanolamine, and thus the lipid emulsion has excellent paclitaxel-encapsulating ability and is stable in blood.

BRIEF DESCRIPTION OF THE DRAWINGS

Other objects, features, and advantages of the present invention will become apparent from the following examples with reference to the accompanying drawings, in which.

DETAILED DESCRIPTION OF THE INVENTION

Figure 1:
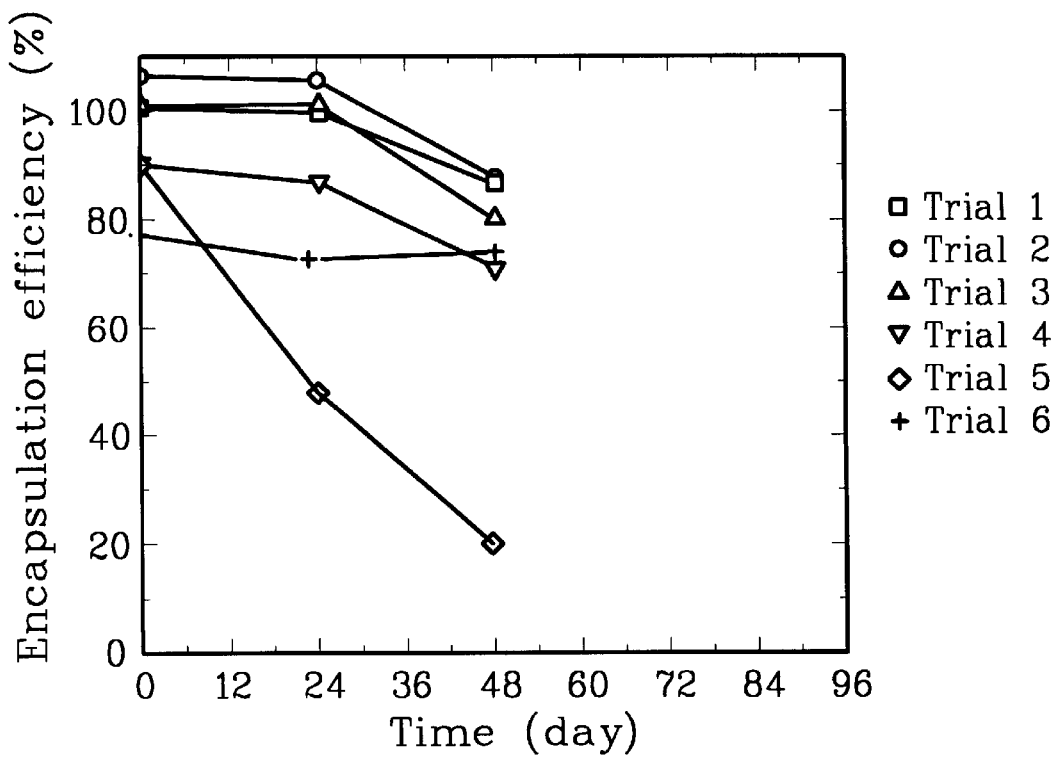
FIG. 1 is a graph showing the percentage of taxol encapsulation (encapsulation efficiency) in lipid emulsions Nos. 1–6 after long-term storage at 4° C.
Figure 2:
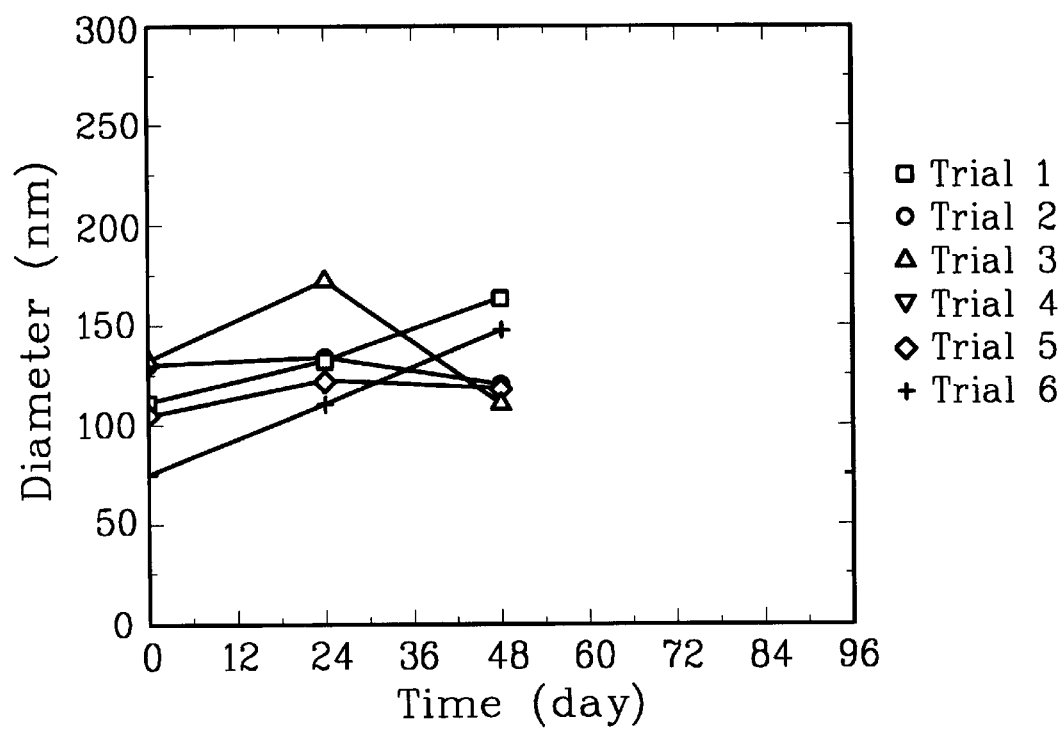
FIG. 2 is a graph showing the particle size stability of lipid emulsions Nos. 1–6 after long-term storage at 4° C.
Figure 3:
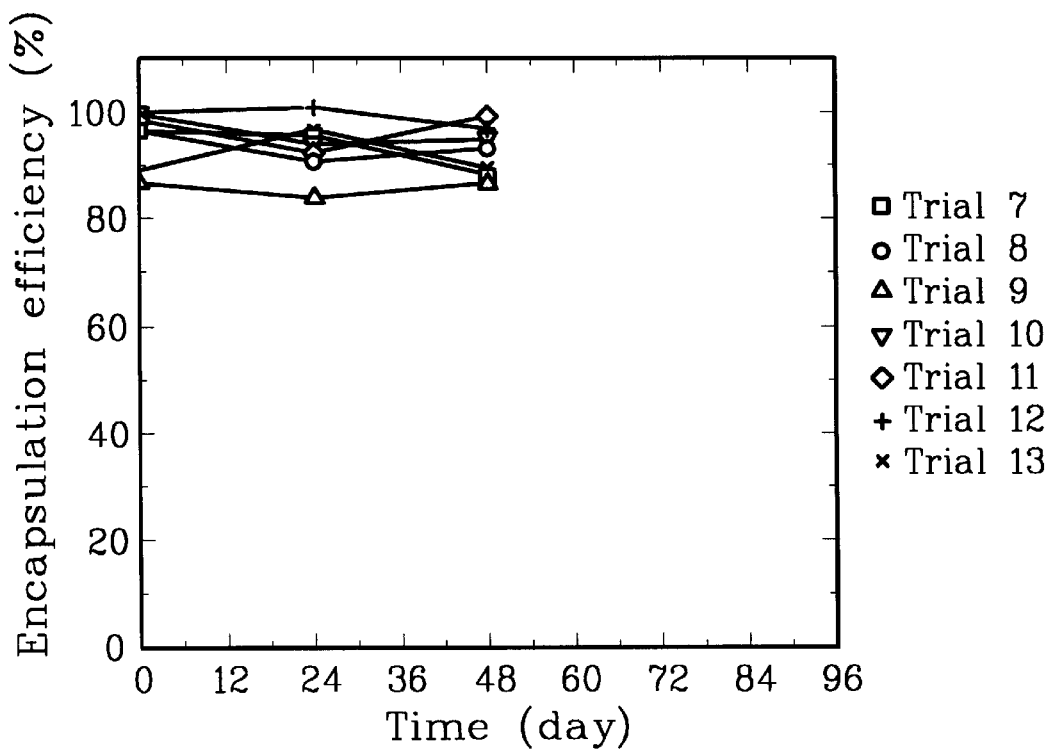
FIG. 3 is a graph showing the percentage of taxol encapsulation (encapsulation efficiency) in lipid emulsions Nos. 7–13 after long-term storage at 4° C.
Figure 4:
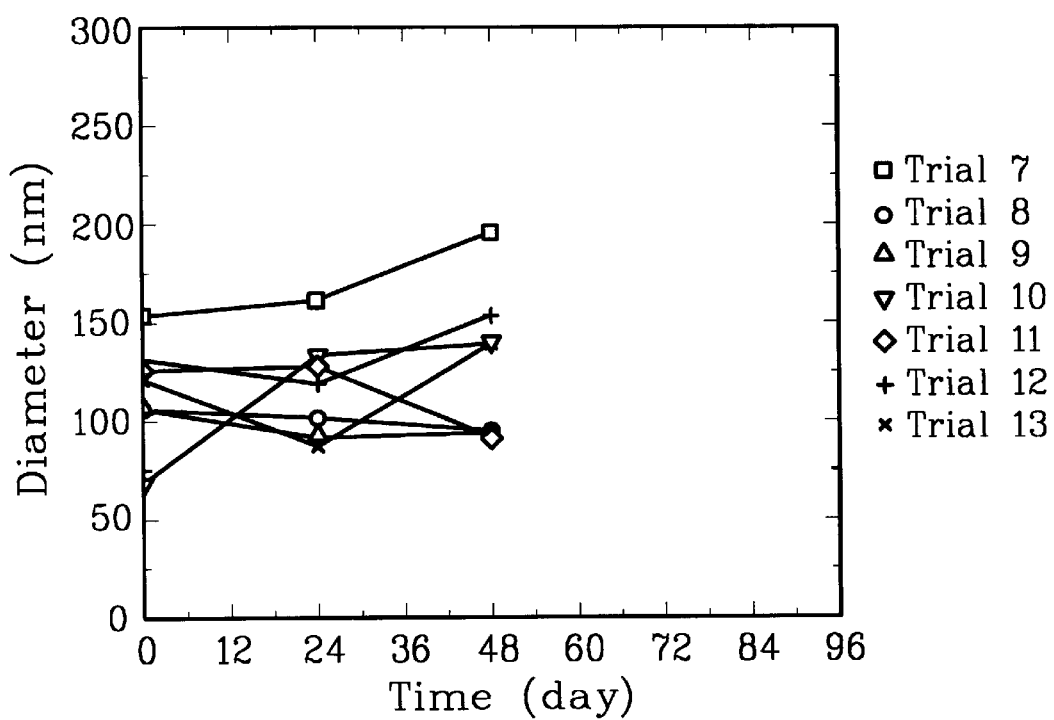
FIG. 4 is a graph showing the particle size stability of lipid emulsions Nos. 1–6 after long-term storage at 4° C.

The oil-in-water emulsion of the invention can be prepared by vigorously mixing triglyceride, emulsifier and paclitaxel in pharmaceutically acceptable aqueous solution, followed by filtering. Specifically, triglyceride, emulsifiers and paclitaxel are first dissolved in a suitable solvent such as chloroform or methanol to obtain a homogeneous solution. The organic solution is then removed and the pharmaceutically acceptable aqueous solution is added. The resulting solution is then vigorously oscillated by using for example a vortex, followed by filtering to obtain an emulsion in which the paclitaxel is encapsulated therein. According to the invention, the concentration of the paclitaxel in the emulsion can reach 0.75–1.75 mg/ml.

The triglyceride is used as the core lipid and is a triglyceride of saturated or unsaturated $C_6$–$C_{18}$ fatty acid, and is preferably tricaproin or tricaprylin. A mixture of tricaproin and tricaprylin in a ratio of 3:1 (w/w) is more preferable.

The weight ratio between core lipid and the emulsion is preferably from 1:0.6 to 1:1.5, and more preferably ranges from 1:1 to 1:1.5.

The weight ratio between phosphatidyl cholin and non-ionic surfactant is preferably from 1:0.3 to 1:1, and more preferably 1:0.5.

The weight ratio among phosphatidyl cholin, non-ionic surfactant and polyethyleneglycol-modified disteaoyl phosphatidylethanolamine is preferably 1:0.4–1:0.1–0.2, and more preferably 1:0.5:0.12.

The pharmaceutically acceptable aqueous solution can be glycerol solution, glucose solution and physiological saline solution. A 2.5% glycerol solution is preferred.

The non-ionic surfactant can be Tween 80, Tween 20 and Pluronic F68. Tween 80 is preferred according to the invention.

The polyethyleneglycol-modified phosphatidylethanolamine is a phosphatidylethanolamine treated by polyethyleneglycol. Preferably, the polyethylene glycol has a molecular weight between 600 and 5000, more preferably a molecular weight of about 2000. Moreover, the preferred polyethyleneglycol-modified phosphatidylethanolamine is polyethylene-modified disteraoyl phosphatidylethanolamine.

Without intending to limit it in any manner, the present invention will be further illustrated by the following examples.

EXAMPLE 1

0.15 g of tricaproin, 0.05 g of tricaprylin, 184 mg of phosphatidyl cholin, 92 mg of Tween 80, 22 mg of polyethyleneglycol-modified disteaoyl phosphatidylethanolamine, and 1.5–3.5 mg of paclitaxel were added in a beaker. Chloroform and methanol were then added into the beaker and mixed intensively to obtain a homogeneous liquid phase. The organic solvents were then removed by evacuating the beaker at 40° C. The mixture formed an even thin film on the wall of the beaker. After the organic solvents were removed completely, 2 ml of 2.5% glycerol solution was added and the opening of the beaker was sealed. The resulting mixture was then oscillated by using vortex for a few seconds to form large emulsion droplets. Thereafter, the beaker was sequentially oscillated in a water-bath ultrasonic oscillator at 25° C. for 10 minutes and in an ultrasonic device at 40° C. for 20 minutes. The mixture was then pressurized to pass through a 0.22 $\mu$m filter membrane to obtain a lipid emulsion droplets dissolved in 2.5% glycerol solution. The concentration of each ingredients of the emulsion is summarized in Table 1 and Table 2 below, in which in Table 1 the weight ratio between core lipid and emulsifier is 1:1 (w/w), while in Table 2 the weight ratio between core lipid and emulsifier is 1:1.5 (w/w).

1 ml of the above 2.5% glycerol solution (containing lipid emulsion droplets) was then added into a centrifugal tube, and centrifuged at 10000 rpm for 2 minutes by a high speed centrifugal separator. The un-encapsulated paclitaxel crystallized and precipitated at the bottom of the centrifugal tube. 2.5 ml of the supernatant was then pippeted carefully to a flask. Water was then removed by using a vacuum concentrator. The concentrate was dissolved in 1 ml of methanol and filtrated through a 0.2 $\mu$m filter. The encapsulated paclitoxel was assayed by HPLC by using a C-18 column, mobile phase: methanol: water=7:3, flow rate: 0.5 ml/min, wavelength: 229 nm. The results are also shown in Table 1 and Table 2.

TABLE 1

| Lipid emulsion | | Concentration (mg/ml) in 2.5% glycerol solution | | | | | |
|---|---|---|---|---|---|---|---|
| NO. | | 1 | 2 | 3 | 4 | 5 | 6 |
| core lipid | tri-caproin | 75 | 75 | 75 | 75 | 75 | 75 |
| | tri-caprylin | 25 | 25 | 25 | 25 | 25 | 25 |
| Emulsifier | PC | 62 | 62 | 62 | 62 | 62 | 62 |
| | Tween 80 | 31 | 31 | 31 | 31 | 31 | 31 |
| | PEG-M-DSPE | 7.4 | 7.4 | 7.4 | 7.4 | 7.4 | 7.4 |
| Paclitaxel | | 0.75 | 0.875 | 1 | 1.25 | 1.5 | 1.75 |
| Encapsulation efficiency | | 100% | 100% | 100% | 90% | 90% | 80% |

TABLE 2

| Lipid emulsion | | Concentration (mg/ml) in 2.5% glycerol solution | | | | | |
|---|---|---|---|---|---|---|---|
| No. | | 7 | 8 | 9 | 10 | 11 | 12 |
| Core lipid | tri-caproin | 75 | 75 | 75 | 75 | 75 | 75 |
| | Tri-caprylin | 25 | 25 | 25 | 25 | 25 | 25 |
| Emulsifier | PC | 92 | 92 | 92 | 92 | 92 | 92 |
| | Tween 80 | 46 | 46 | 46 | 46 | 46 | 46 |
| | PEG-M-DSPE | 11 | 11 | 11 | 11 | 11 | 11 |
| Paclitaxel | | 0.75 | 0.875 | 1 | 1.25 | 1.5 | 1.75 |
| Encapsulation efficiency | | 100% | 100% | 100% | 90% | 90% | 80% |

As can be seen from Table 1 and Table 2, the lipid emulsion droplets have an encapsulation efficiency larger than 80% with respect to 0.75–1.5 mg/ml paclitaxel.

EXAMPLE 2

Lipid emulsions Nos. 1–12 of Example 1 were placed at a temperature of 4° C. for several days. The encapsulation efficiency of paclitaxel thereof were measured and the diameter of the droplets of oil-in-water emulsions were also measured by laser light scatting. The results are shown in FIG. 1, FIG. 2, FIG. 3, and FIG. 4 respectively.

AS indicated in these figures, except lipid emulsion No. 5, the paclitaxel's encapsulation efficiency and the particle size of the droplets can be held constant and stable even after 24-day storage at 4° C.

EXAMPLE 3

In this example, the encapsulation efficiency and diameter stability between lipid emulsion No. 12 of Example 1, a conventional non-modified lipid emulsion (No. 13), and Diluent 12 (No. 14) with 30 times fetal calf serum (FCS) at 37° C. were measured.

Figure 5:
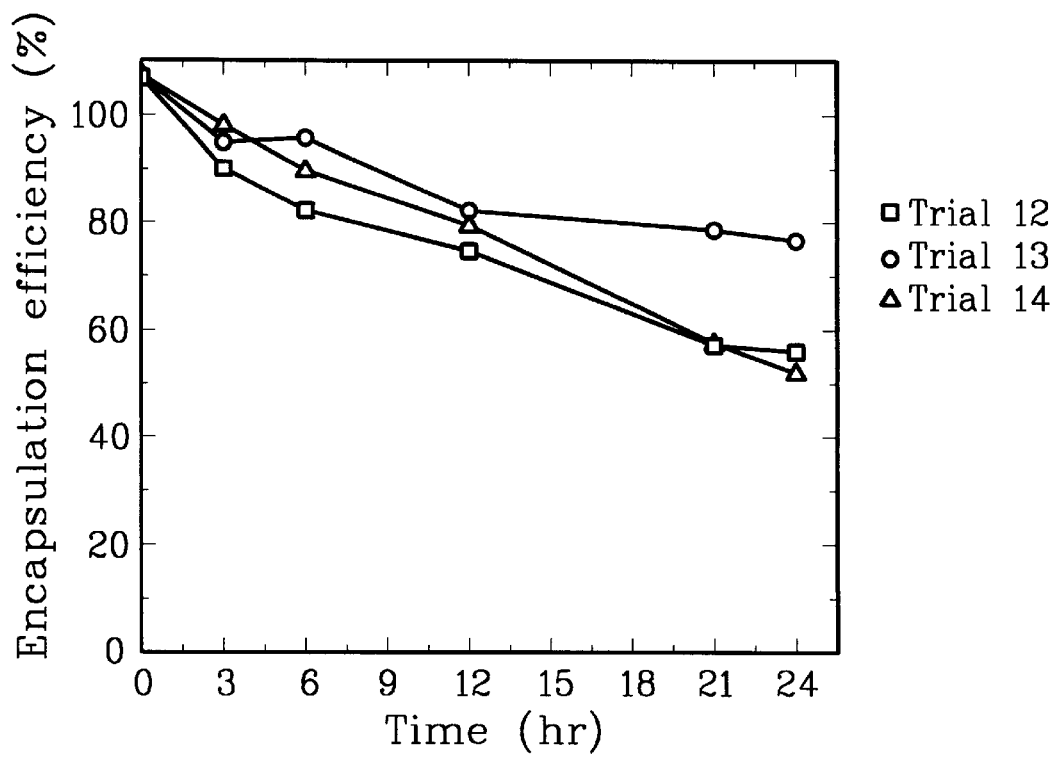
FIG. 5 is a graph showing the comparison of taxol encapsulation efficiency between lipid emulsions Nos. 12, 13 and 14 with 30 times fetal calf serum at 37° C.
Figure 6:
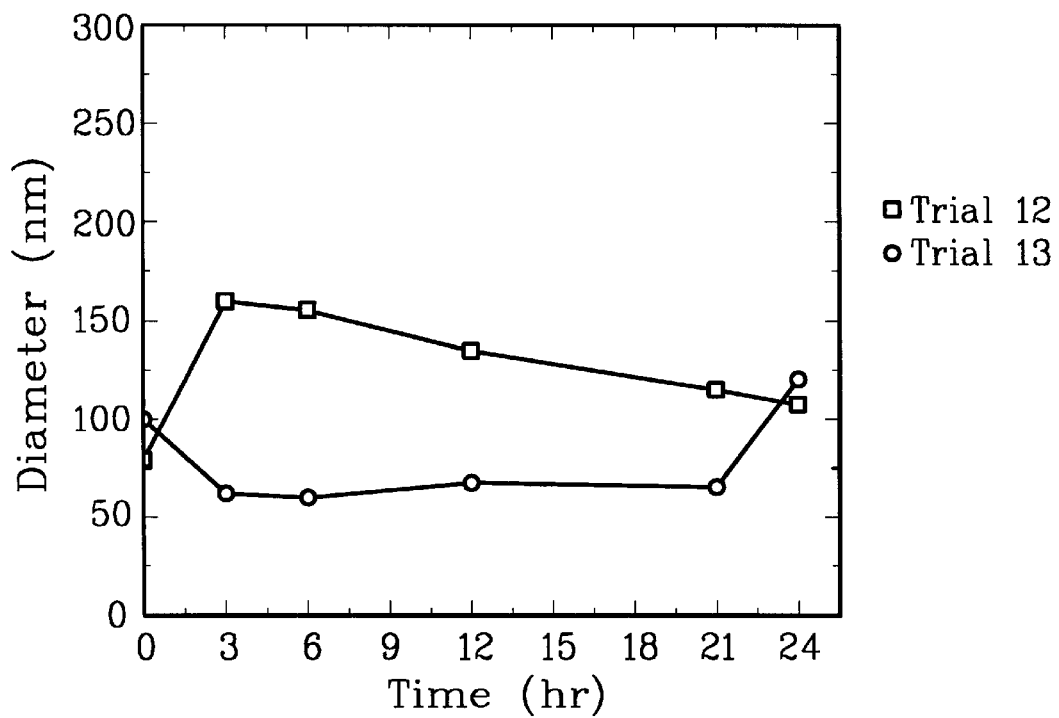
FIG. 6 is a graph showing the lipid emulsion diameter stability between lipid emulsions Nos. 12, 13 and 14 with 30 times fetal calf serum at 37° C.

The above three emulsions were diluted with 30 times FCS, and then the diluted solutions were placed in a reciprocating thermostat. The thermostat was maintained at a temperature of 37° C., and was rotated at a speed of 70 rpm. The thermostat was also covered with a lid to shield from irradiation by light. The encapsulation efficiencies were measured by the following procedures. 1 ml of the above diluted emulsions was sampled and centrifuged. 0.5 ml of supernatant were taken and the water was removed by vacuum concentrator. After the water was evaporated, 1.5 ml of methanol was added thereto to denature the proteins in serum and precipitate it. The supernatant was then centrifuged at 3000 rpm for 5 minutes. The paclitaxel in the supernatant was assayed by liquid chromatography and the result is shown in FIG. 5. The particle sizes of the droplets were measured by laser scatting and the results are shown in FIG. 6.

As can be seen from FIG. 5, the encapsulation efficiency of lipid emulsion NO. 12 is larger than that of lipid emulsion No. 13 and lipid emulsion NO. 14. Also, as indicated in FIG. 6, the diameter of the droplets of lipid emulsion No. 12 is smaller than that of lipid emulsion No. 14. Note that because the lipid emulsion No. 14 belongs to micelles, the diameter of the droplets thereof was unable to be measured.

EXAMPLE 4

In this example, the encapsulation efficiency and diameter stability between lipid emulsion No. 12 of Example 1, a conventional non-modified lipid emulsion (No. 13), and Diluent 12 (No. 14) with 30 times phosphate buffer at 37° C. were measured.

Figure 7:
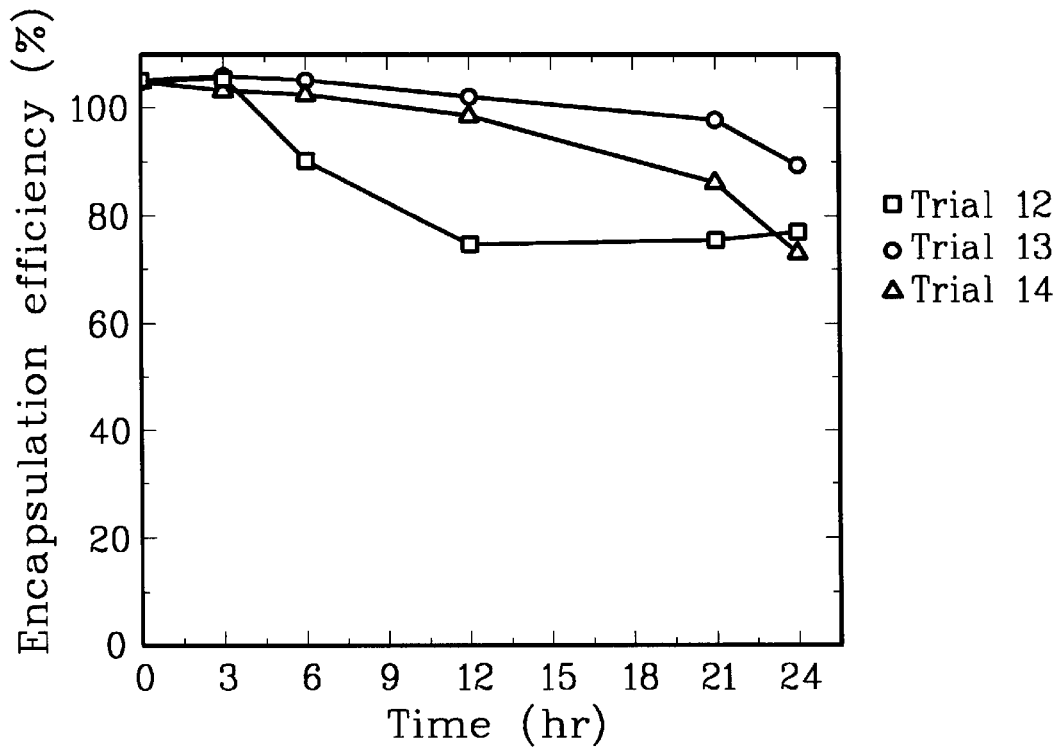
FIG. 7 is a graph showing the comparison of taxol encapsulation efficiency between lipid emulsions Nos. 12, 13 and 14 with 30 times phosphate buffer at 37° C.
Figure 8:
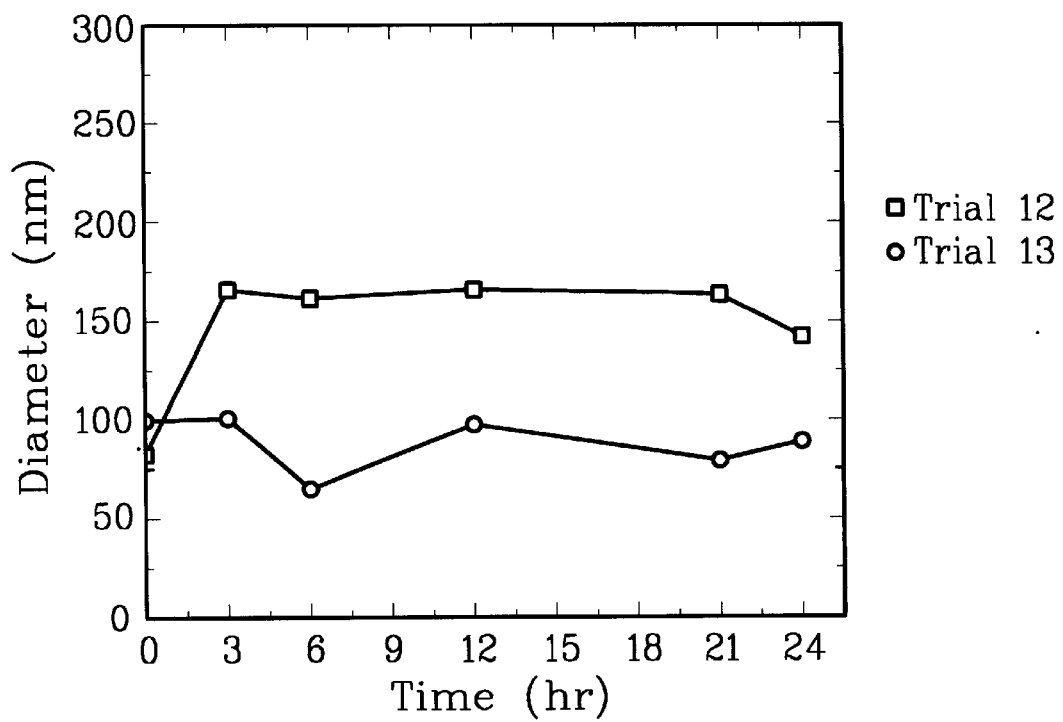
FIG. 8 is a graph showing the lipid emulsion diameter stability between lipid emulsions Nos. 12, 13 and 14 with 30 times phosphate buffer at 37° C.

The above three emulsions were diluted with 30 times phosphate buffer, and then the diluted solutions were placed in a reciprocating thermostat. The thermostat was maintained at a temperature of 37° C., and was rotated at a speed of 70 rpm. The thermostat was also covered with a lid to shield from irradiation by light. The encapsulation efficiencies were measured by the same procedures as in Example 3 and the results are shown in FIG. 7. The particle sizes of the droplets was also measured by laser scatting and the results are shown in FIG. 8.

As can be seen from FIG. 7, the encapsulation efficiency of lipid emulsion NO. 12 is larger than that of lipid emulsion No. 13 and lipid emulsion NO. 14. Also as indicated in FIG. 8, the diameter of the droplets of lipid emulsion No. 12 is smaller than that of lipid emulsion No. 14. Note that because the lipid emulsion No. 14 belongs to micelles, the diameter of the droplets thereof was unable to be measured.

While the invention has been particularly shown and described with the reference to the preferred embodiment thereof, it will be understood by those skilled in the art that various changes in form and details may be made without departing from the spirit and scope of the invention.

What is claimed is:

1. An oil-in-water emulsion for encapsulating paclitaxel comprising:

triglyceride;

emulsifier comprising phosphatidyl choline, non-ionic surfactant and polyethyleneglycol-modified phosphatidylethanolamine; and pharmaceutically acceptable aqueous solution;

wherein the weight ratio of said triglyceride and said emulsifier ranges between 1:1 to 1:1.5 and said triglyceride is homogeneously dispersed in said pharmaceutically acceptable aqueous solution.

2. The oil-in-water emulsion as claimed in claim 1, wherein said triglyceride is a triglycerides of saturated or unsaturated $C_6$–$C_{18}$ fatty acid.

3. The oil-in-water emulsion as claimed in claim 2, wherein said triglyceride is selected from the group consisting of tricaproin, tricaprylin, and the mixtures thereof.

4. The oil-in-water emulsion as claimed in claim 3, wherein said triglyceride is a mixture of tricaprylin and tricaproin in a ratio of 1:3 (w/w).

5. The oil-in-water emulsion as claimed in claim 1, wherein said non-ionic surfactant is selected from the group consisiting of Tween 20, Tween 80 and Pluronic F68.

6. The oil-in-water emulsion as claimed in claim 1, wherein said polyethyleneglycol-modified phosphatidylethanolamine is polyethyleneglycol-modified disteaoyl phosphatidylethanolamine.

7. The oil-in-water emulsion as claimed in claim 6, wherein the molecular weight of said polyethyleneglycol ranges between 600 to 5000.

8. The oil-in-water emulsion as claimed in claim 7, wherein the molecular weight of said polyethyleneglycol is 2000.

9. The oil-in-water emulsion as claimed in claim 1, wherein the weight ratio among said phosphatidyl choline, non-ionic surfactant and polyethyleneglycol-modified phosphatidylethanolamine is 1:(0.4–1):0.12.

10. The oil-in-water emulsion as claimed in claim 1, wherein said pharmaceutically acceptable aqueous solution is selected from the group consisting of glycerol solution, glucose solution and physiological saline solution.

11. The oil-in-water emulsion as claimed in claim 10, wherein said pharmaceutically acceptable aqueous solution is a 2.5% glycerol solution.

12. The oil-in-water emulsion as claimed in claim 1, wherein the concentration of said paclitaxel ranges between 0.75 to 1.5 mg/ml.

13. An oil-in-water emulsion for encapsulating pacLitaxel comprising:

triglyceride; and emulsifier comprising phosphatidyl choline, non-ionic surfactant and polyethyleneglycol-modified phosphatidylethanolamine; wherein the weight ratio between said triglyceride and said emulsifier ranges between 1:1 to 1:1.5.

14. The oil-in-water emulsion as claimed in claim 13, wherein said triglyceride is a triglyceride of saturated or unsaturated $C_6$–$C_{18}$ fatty acid.

15. The oil-in-water emulsion as claimed in claim 14, wherein said triglyceride is selected from the group consisting of tricaproin, tricaprylin, and the mixtures thereof.

16. The oil-in-water emulsion as claimed in claim 15, wherein said triglyceride is a mixture of tricaproin and tricaprylin in a ratio of 1:3 (w/w).

17. The oil-in-water emulsion as claimed in claim 13, wherein said non-ionic surfactant is selected from the group consisting of Tween 20, Tween 80 and Pluronic F68.

18. The oil-in-water emulsion as claimed in claim 13, wherein said polyethyleneglycol-modified phosphatidylethanolamine is polyethyleneglycol-modified disteaoyl phosphatidylethanolamine.

19. The oil-in-water emulsion as claimed in claim 18, wherein the molecular weight of said polyethyleneglycol ranges between 600 to 5000.

20. The oil-in-water emulsion as claimed in claim 19, wherein the molecular weight of said polyethyleneglycol is 2000.

21. The oil-in-water emulsion as claimed in claim 13, wherein the weight ratio among said phosphatidyl choline, non-ionic surfactant and polyethyleneglycol-modified phosphatidylethanolamine in said emulsion is 1:(0.4–1):0.12.

* * * * *